US006416750B1

(12) United States Patent
Harper et al.

(10) Patent No.: US 6,416,750 B1
(45) Date of Patent: Jul. 9, 2002

(54) LOW TEMPERATURE PROCESS FOR MAKING STABLE ANHYDROUS SOLUTIONS OF ANTIPERSPIRANT ACTIVE IN SELECTED 1,2-DIOL SOLVENTS

(75) Inventors: Thomas Lee Harper, Middletown; Shailesh Mehta, Port Jervis, both of NY (US); Allan Herbert Rosenberg, South Orange, NJ (US)

(73) Assignee: Somerville Technology Group, Inc., Huguenot, NY (US)

( * ) Notice: Subject to any disclaimer, the term of this patent is extended or adjusted under 35 U.S.C. 154(b) by 0 days.

(21) Appl. No.: 09/862,605

(22) Filed: May 23, 2001

(51) Int. Cl.$^7$ .............. A61K 7/32; A61K 7/34; A61K 7/38; A61K 7/00
(52) U.S. Cl. .............. 424/65; 424/66; 424/68; 424/400; 424/401
(58) Field of Search .............. 424/65, 66, 68, 424/400, 401

(56) References Cited

U.S. PATENT DOCUMENTS 4,781,917 A * 11/1988 Luebbe et al. ............. 424/65
5,463,098 A * 10/1995 Giovanniello et al. ...... 424/66
5,643,558 A *  7/1997 Provaneal et al. .......... 424/66

* cited by examiner

Primary Examiner—Shelley A. Dodson
(74) Attorney, Agent, or Firm—Kenneth P. Glynn, Esq.

(57) ABSTRACT

Disclosed is process of making stable antiperspirant active solutions, which process comprises the steps of: (A) preparing an aqueous solution comprising an aluminum-containing antiperspirant active, water, and an anhydrous solvent having a solubility parameter of from about 9 $(cal/cm^3)^{0.5}$ to about 15 $(cal/cm^3)^{0.5}$; (B) spray-drying the aqueous solution to form a solid powder comprising aluminum-containing antiperspirant active and the anhydrous solvent; and (C) dissolving the solid powder in a second anhydrous solvent at a temperature of not more than 85° C., the second anhydrous solvent comprising a 1,2-diol solvent having at least 4 carbon atoms, to form a stable antiperspirant active solution comprising solubilized aluminum-containing antiperspirant active and the 1,2-diol solvent. The stable antiperspirant active solutions are especially useful as manufacturing intermediate materials that provide improved formulation flexibility when preparing antiperspirant consumer products, especially those products that are clear or translucent in appearance.

22 Claims, No Drawings

LOW TEMPERATURE PROCESS FOR MAKING STABLE ANHYDROUS SOLUTIONS OF ANTIPERSPIRANT ACTIVE IN SELECTED 1,2-DIOL SOLVENTS

TECHNICAL FIELD

The present invention relates to a low temperature process for making stable anhydrous solutions of aluminum-containing antiperspirant active in selected polyol solvents.

BACKGROUND OF THE INVENTION

There are many antiperspirant products commercially available or otherwise known for use in controlling or inhibiting underarm perspiration and odor. These formulations typically contain an antiperspirant active material such as an aluminum or zirconium salt in a suitable carrier such as an aqueous or alcohol solvent. The antiperspirant active can be in the form of solid dispersed particulates or solubilized with a solvent matrix.

Clear antiperspirant products have become increasingly popular among consumers over the past several years. These products typically contain antiperspirant active materials solubilized in a suitable liquid carrier. These compositions can be aqueous or anhydrous, but are often formulated as anhydrous formulations to provide drier skin feel during and after application to the underarm. Solubilized antiperspirant actives in anhydrous systems are most typically solubilized with solvents such as ethanol, propylene glycol, polyethylene glycols, and other monohydric or polyhydric materials.

One method for making solubilized antiperspirant active for use in antiperspirant products begins with the preparation of antiperspirant active solutions containing water, polyhydric alcohols, and an aluminum-containing active or aluminum and zirconium-containing active. These aqueous polyhydric alcohol solutions are then subjected to spray drying or other rapid drying method to thus form substantially anhydrous powders containing aluminum or aluminum and zirconium active and polyhydric alcohol associated with or otherwise bound to the active material within the powders. These spray dried powders are then combined with a suitable solvent, most typically a polyol solvent such as propylene glycol, at solvent temperatures generally exceeding about 90° C., to thus form a finished or intermediate antiperspirant product containing solubilized antiperspirant active.

It has now been found, however, that the above-described process for making solubilized antiperspirant active can be improved by using low temperature solubilization of the spray dried active in a polyol solvent. This can be accomplished by 1) selecting the polyol or other anhydrous solvent added to the antiperspirant active prior to spray drying, 2) selecting certain polyol solvents that are then added to the spray dried antiperspirant active to solubilize the spray dried solid, and 3) maintaining solvent solubilization temperatures after spray drying of less than about 85° C. The first selected polyol or anhydrous solvent must have a solubility parameter of from about 9 $(cal/cm^3)^{0.5}$ to about 15 $(cal/cm^3)^{0.5}$, whereas the second selected polyol solvent that solubilizes the spray dried material must be a 1,2-diol having at least 4 adjacent carbon atoms. The lower solubilization temperatures after spray drying allow for less energy intensive processing and improved processing and formulation flexibility, especially when processing or formulating with relatively heat-labile materials.

SUMMARY OF THE INVENTION

The present invention is directed to a process of making stable anhydrous antiperspirant active solutions, which process comprises the steps of: (A) preparing an aqueous antiperspirant active solution comprising an aluminum-containing antiperspirant active, water, and an anhydrous solvent having a solubility parameter of from about 9 $(cal/cm^3)^{0.5}$ to about 15 $(cal/cm^3)^{0.5}$; (B) spray-drying the aqueous solution to form a solid powder comprising aluminum-containing antiperspirant active and the anhydrous solvent; and (C) dissolving the solid powder in a second anhydrous solvent at a temperature of not more than about 85° C., the second anhydrous solvent comprising a 1,2-diol solvent having at least 4 carbon atoms, to thereby form a stable anhydrous antiperspirant active solution comprising solubilized aluminum-containing antiperspirant active and the 1,2-diol solvent.

It has been found that the stable antiperspirant active solutions provided by the process of the present invention are especially useful as manufacturing intermediates in providing improved formulation and process flexibility when preparing antiperspirant consumer products, especially those products that are clear or translucent in appearance. It has been found that the selection of the anhydrous solvent used in the spray-drying step (selected solubility parameter) and the polyol solvent used in the active dissolution (1,2-diol have at least 4 adjacent carbon atoms), among the many polyol and anhydrous solvents known in the antiperspirant formulation art, allow for low temperature dissolution of the spray dried antiperspirant active and improved formulation and manufacturing flexibility in preparing a clear or low residue antiperspirant product containing solubilized antiperspirant active.

DETAILED DESCRIPTION

The process of the present invention, including essential and optional characteristics thereof, are described in detail hereinafter. All percentages, parts and ratios as used herein are by weight of the total referenced composition, unless otherwise specified. All such weights as they pertain to listed ingredients are based on the active level and, therefore, do not include solvents or by-products that may be included in commercially available materials, unless otherwise specified.

The term "anhydrous" as used herein, unless otherwise specified, means that the referenced material or composition contains less than about 20%, preferably less than about 10%, more preferably less than about 5%, most preferably zero percent, by weight of water.

The process of the present invention can comprise, consist of, or consist essentially of the essential elements and limitations of the invention described herein, as well as any additional or optional ingredients, components, or limitations described herein or otherwise useful in antiperspirant applications.

PROCESS

The process of the present invention provides a more efficient or alternative method for making anhydrous antiperspirant compositions comprising solubilized antiperspirant active. The anhydrous antiperspirant compositions made in accordance with the process of the present invention can be used as finished antiperspirant products for consumer application, or as manufacturing intermediates to formulate any of a variety of anhydrous antiperspirant products containing solubilized antiperspirant active or other antiperspirant active derived from solubilized antiperspirant active.

A) Preparation of Aqueous Active Solution

The first step of the process of the present invention is the preparation of an aqueous antiperspirant active solution comprising an aluminum-containing antiperspirant active, water and an anhydrous solvent having a solubility parameter of from about 9 $(cal/cm^3)^{0.5}$ to about 15 $(cal/cm^3)^{0.5}$. Many such aqueous antiperspirant active solutions are commercially available and an be used in the process herein, or such aqueous solutions can be prepared by methods well known or otherwise described in the antiperspirant arts for making solubilized aluminum-containing antiperspirant active, non-limiting examples of which include U.S. Pat. No. 5,463,098 Giovanniello et al.); U.S. Pat. No. 5,643,558 (Provancal et al.); U.S. Pat. No. 4,781,917 (Luebbe et al.); which descriptions are incorporated herein by reference.

The first step of the process of the present invention is the obtaining or otherwise preparing of an aqueous antiperspirant active solution preferably having from about 5% to about 90%, more preferably from about 20% to about 60%, by weight of an anhydrous solvent having the requisite solubility parameter; preferably from about 5% to about 70%, more preferably from about 5% to about 50%, by weight of water; and preferably from about 5% to about 40%, more preferably from about 10% to about 30%, by weight of the aluminum-containing antiperspirant active.

The first step of the process herein most preferably involves the combination of aluminum metal, hydrochloric acid and water, followed by heating of the combination at a temperature above 50° C., more preferably from about 70° C. to about 100° C., for at least about two hours, more preferably for at least about 10 hours, even more preferably from about 15 to about 21 hours, to obtain the desired aluminum polymer size distribution resulting from the prolonged heating process. It is understood, however, that heating during the first step is not required of the process of the present invention, or is not otherwise required to the extent and duration described above for those embodiments in which the desired polymer size distribution is obtained earlier or does not otherwise require such prolonged heating to achieve. Generally, prolonged heating during the initial process step results in enhanced efficacy active, whereas little or no heating will result in less effective active, both of which can be used in the process of the present invention. The additional heating step is preferred for use herein. Although less preferred, the heat activation of the aluminum-containing active solution can be achieved after optionally mixing the solution with a zirconium-containing active solution as described hereinafter.

The aluminum-containing antiperspirant active for use in the process of the present invention includes any inorganic or organic aluminum salt, preferably an aluminum halide, aluminum chlorohydrate, aluminum hydroxyhalides, or mixtures thereof. Suitable aluminum salts for use in this manner include those aluminum salts which conform to the formula:

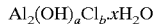

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide" wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald at al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

The anhydrous solvent for use in the first step of the process of the present invention is selected so as to have a solubility parameter of from about 9 $(cal/cm^3)^{0.5}$ to about 15 $(cal/cm^3)^{0.5}$, preferably from about 10 $(cal/cm^3)^{0.5}$ to about 13 $(cal/cm^3)^{0.5}$. Any anhydrous material is suitable for use in the first process step herein provided that it has the requisite solubility parameter, is compatible with the other essential or selected ingredients used in the process, and is otherwise suitable for manufacturing materials intended for topical application to the skin. Non-limiting examples of such suitable anhydrous solvents include ethylene glycol, propylene glycol, polyethylene glycols, dipropylene glycol, diethylene glycol, butylene glycol, 1,2-pentanediol, hexylene glycol, 1,2-propylene glycol, 1,3-propylene glycol, 1,2-hexanediol, 2-ethyl-1,3-hexanediol, 1,2,6-hexanetriol, ethanol, hexylene glycol, polypropylene glycols, tripropylene glycol, propylene glycol methyl ether, isopropyl glyerol ether, dipropylene glycol methyl ether and combinations thereof. Preferred are butylene glycol, polyethylene glycol, and combinations thereof. Other suitable anhydrous solvents include many of the polar solvents described in U.S. Pat. No. 5,429,816, which descriptions are incorporated herein by reference.

The solubility parameter of various materials, including the anhydrous solvent for use herein, can be destined by methods well known in the various chemical arts for determining such parameter values, some methods of which are described by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988, which descriptions are incorporated herein by reference.

B) Stray Drying Step

The second step in the process of the present invention is the spray drying step in which the aqueous antiperspirant active solution prepared by the first step of the process of the present invention is transformed by spray drying to form a solid powder. The resulting spray dried powder comprises from about 10% to about 40% by weight of the aluminum-containing antiperspirant active, from about 5% to about 40% by weight of the anhydrous solvent, and from about 5% to about 20% by weight of water.

The second step in the process of the present invention may further comprise the combining of a zirconium-containing active solution with the aluminum-containing active solution prior to or during the spraying drying process. In the event that the aluminum-containing active solution is subjected to prolonged heating prior to spray drying to enhance efficacy, it is preferred that the zirconium-containing active be combined with the aluminum-containing active after such prolonged heating. The atomic ratio of aluminum to zirconium in the resulting combination is preferably from about 10:1 to about 1:10, more preferably from about 6:1 to about 1:6, even more preferably from about 3:1 to about 1:6.

The zirconium-containing active solution for use in the process of the present invention is preferably an aqueous solution comprising from about 5% to about 50%, more preferably from about 10% to about 35%, by weight of zirconium-containing active. The zirconium-containing active solution also preferably comprises from about 5% to about 90%, more preferably from about 20% to about 60%, by weight of an anhydrous solvent as described hereinbefore and having a solubility parameter of from about 9 $(cal/cm^3)$ $^{0.5}$ to about 15 (cal/cm$^3$)$^{0.5}$. The anhydrous solvent for use with the aluminum-containing active solution can in fact be obtained in whole or in part from the zirconium-containing active solution, such that the aluminum-containing active solution prior to combining with the zirconium-containing active solution can be an aqueous solution containing some or no anhydrous solvents as described hereinbefore. It is understood, however, that either or both of the aluminum-containing solution or the zirconium-containing solution prior to mixing and spray drying may contain the requisite anhydrous solvent, or the solvent may be formulated into the process from neither of the metal solutions but rather from a third solution or material that is combined with the metal solutions prior to or during the spray drying sequence.

The zirconium-containing active for use in the process of the present invention include those materials that conform to the formula:

$$ZrO(OH)_{2-a}Cl_a \cdot xH_2O$$

wherein a is any number having a value of from 0 to about 2; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4.120,948, Shelton, issued Oct. 17, 1978, all of which are incorporated herein by reference.

Neutral amino acids such as glycine are preferably added to the zirconium-containing solution prior to spray drying, but can be added to the aluminum-containing solutions prior to spray drying as well, to thus form an amino acid complex with the aluminum-containing active, the zirconium-containing active, or the aluminum-zirconium-containing active. The neutral amino acid is preferably added to provide an aluminum (or aluminum and zirconium) to neutral amino acid weight ratio of from about 0.25:1 to about 5:1, more preferably from about 0.5:1 to about 2:1. The pH of the aluminum-containing active solutions, zirconium-containing active solutions, and zirconium-aluminum active solutions throughout the process of the present invention should be maintained to within a pH range of from about 2 to about 5.

C) Low Temperature Dissolution

The process of the present invention further comprises a low temperature dissolution step in which the spray dried antiperspirant active is combined with selected polyol solvents at a temperature of not more than 85° C. The added solvents help to solubilize the spray-dried active to form a solubilized aluminum-containing antiperspirant active solution suitable for use as a finished antiperspirant consumer product, or as a manufacturing intermediate for use in preparing finished antiperspirant consumer products containing or derived from solubilized antiperspirant active.

The low temperature dissolution step comprises the combining or mixing of the spray dried antiperspirant active with a polyol solvent that is a 1,2-diol having at least four adjacent carbon atoms, wherein the carbon atoms at the α and β positions of the adjacent carbons have attached hydroxy moieties. The 1,2-diol solvent is preferably a liquid under ambient conditions or is otherwise in liquid form as formulated within the finished composition. Solvent temperatures during the dissolution step must not exceed about 85° C. and preferably range from about 25° C. to about 65° C., more preferably from about 30° C. to about 60° C. The low temperature dissolution is preferably accompanied by agitation or mixing of the spray dried active and the selected 1,2-diol, more preferably high shear mixing, all of which should continue until the spray dried active is completely dissolved, or has otherwise reached a point beyond which further dissolution will not readily occur.

The 1,2-diol is added to the composition in an amount sufficient to provide partial or complete dissolution, preferably complete dissolution, of the spray dried active at the selected dissolution temperature, which should then remain dissolved to the desired extent once the solvent temperature returns to ambient conditions. The 1,2-diol is preferably added to the spray dried active such that the weight ratio of the 1,2-diol solvent to the aluminum or aluminum and zirconium active is from about 1:2 to about 20:1, preferably from about 1:1 to about 10:1, more preferably from about 2:1 to about 4:1.

The 1,2-diol solvents for use in the low temperature dissolution step include those polyols that conform to the formula:

$$HO-CH_2-\underset{\underset{OH}{|}}{CH}-R$$

wherein R is an amide, ester, alkyl, ether or silicone-containing moiety, each moiety containing at least 2 carbon atoms. The R group is preferably an alkyl or ether group, more preferably an alkyl group having from about 2 to about 10 carbon atoms, more preferably from about 4 to about 6 carbon atoms. The liquid polyols preferably have either 2 or 3 hydroxyl groups in total. The R group on the liquid polyol can therefore be substituted or unsubstituted, branched or straight or cyclic, saturated or unsaturated. Non limiting examples of suitable substituents include hydroxy groups, amines, amides, esters, ethers, alkoxylate groups (e.g., ethoxylates, propoxylates, etc.) and so forth.

Non limiting examples of suitable 1,2-diols for use in the process of the present invention include 1,2-butanediol; 1,2-pentanediol; 4-methyl-1,2-pentanediol; 2-methyl-1,2-pentanediol; 3,3-methyl-1,2-butanediol; 4-methyl-1,2-hexanediol; 1,2-heptanediol; 3-phenyl-1,2-propanediol: 1,2,6-hexanetriol; 1,2-hexandiol; 1,2,4-butanetriol: and combinations thereof. Other suitable liquid polyols include glycerol ethers such as glycerol isopropyl ether; glycerol propyl ether; glycerol ethyl ether; glycerol methyl ether; glycerol butyl ether; glycerol isopentyl ether; diglycerol isopropyl ether; diglycerol isobutyl ether; diglycerol; triglycerol; triglycerol isopropyl ether; and combinations thereof. Still other suitable liquid polyols include acetic acid glycerol ester; propanoic acid glycerol ester; butanoic acid glycerol ester; 3-methyl butanoic acid glycerol ester; and 3-trimethylsily-1,2-propane diol; silicone-containing 1,2-diols such as those described in U.S. Pat. No. 5,969,172 (Nye); and combinations thereof.

The resulting antiperspirant active solution made in accordance with the process described herein is an anhydrous system that contains from about 1% to about 40%, more preferably from about 5% to about 26%, even more preferably from about 10% to about 26%, by weight of solubilized aluminum or aluminum and zirconium active, and from about 5% to about 99%, preferably from about 5% to about 50%, by weight of the 1,2-diol solvent.

The anhydrous antiperspirant active solutions made in accordance with the process of the present invention have a preferred metal to chloride atomic ratio of from about 6.73 to about 2.1, from about 1 to about 6 moles of water (water of hydration associated with the metal active) per mole of aluminum salt. For those embodiments of the process of the present invention including the additional use of zirconium containing actives, the resulting anhydrous antiperspirant active solution preferably contains from about 1 to about 7 moles of water (water of hydration associated with the zirconium active) per mole of zirconium salt and from about 1 to about 6 moles of water (water of hydration associated with the aluminum active) per mole of aluminum salt.

The various solutions used in the process of the present invention may further comprise other additional ingredients suitable for use as manufacturing aids, or which are otherwise known or effective for use in topical antiperspirant and deodorant products, provided that such other additional ingredients are compatible with the ingredients of the corresponding solution, or which do not unduly impair the process of the present invention and the intended benefits arising therefrom.

Non limiting examples of optional ingredients for use in the process include pH buffering agents; cosolvents or additional emollients; humectants; soothing agents; dyes and pigments; suspending or thickening agents; residue masking agents; wash-off aids; antimicrobial agents; chelants; perfumes; medicaments or other topical active material; preservatives; and so forth. Other non limiting examples of optional ingredients include those described in U.S. Pat. No. 4,049,792 (Elsnau); U.S. Pat. No. 5,019,375 (Tanner et al.); U.S. Pat. No. 5,429,816 (Hofrichter et al.); which descriptions are incorporated herein by reference.

EXAMPLES

The following Examples illustrates specific embodiments of the process of the present invention, but are not intended to be limiting thereof. Other modifications can be undertaken by the skilled artisan without departing from the spirit and scope of this invention.

Example I

An aqueous solution containing solubilized aluminum-containing antiperspirant active is prepared from the following ingredients: aluminum chlorohydrate (89.94 grams; Al-12.45%, Cl-8.22%); water (10.06 grams); 1,3-butylene glycol (10.00 grams); and PEG 1000 (2.00 grams). The aluminum chlorohydrate (ACH-303), water and 1,3-butylene glycol are combined and mixed together under ambient conditions. Also under ambient conditions, PEG 1000 (wax solid) is then added to the combination and mixed until completely dissolved. The resulting aqueous antiperspirant active solution is then immediately (i.e., within 0–2 hours after preparation) subjected to spray drying on a Buchi 190 Mini Spray Dryer (Brinkman Instruments, Westbury, N.Y., USA) with an outlet temperature of from 88° C. to 90° C. and an inlet temperature that remains at about 237° C. The feed and other spray drying parameters are controlled to maintain the desired outlet temperature. The spray dried product or crystals are collected in a receiver. The collected product has a chloride content of from 14.42% to 14.58% by weight of the collected product.

The spray dried product is then combined with 1,2-hexanediol under ambient conditions and subjected to high shear mixing for a period of about 16 hours. The resulting mixture is allowed to stand for several hours before filtering out any remaining solids to form a light yellow colored transparent solution. Various combinations of spray dried product and 1,2-hexanediol are mixed together to anhydrous aluminum-containing active solutions having varied active concentrations at 1%, 5%, 10%, 15%, 20% and 26%, by weight of the anhydrous solution.

All of the above dissolution process steps for the various active concentrations are repeated but without high shear mixing, but each dissolution under such conditions takes substantially longer than with high shear mixing.

All of the above dissolution process steps for the various active concentrations are also repeated by heating the dissolution solvent (1,2-hexanediol) to between 40° C. and 60° C. to reduce the dissolution time to substantially less than 16 hours.

All of the anhydrous aluminum-containing antiperspirant active solutions exemplified above are applied topically to the underarm area of the skin as a finished antiperspirant consumer product to provide antiperspirant and deodorant efficacy to the applied area of the skin. The applied compositions are clear or translucent, provide little or no visible residue during and after application. All of the exemplified solutions are also used as manufacturing intermediates in formulating finished antiperspirant consumer products comprising solubilized antiperspirant active in solid, semi-solid and liquid forms.

Example II

An aqueous solution containing solubilized aluminum-containing antiperspirant active is prepared which contains aluminum chlorohydrate (60.67 grams, Al-13.22%, Cl-8.54%); water (82.24 grams); and hydrochloric acid solution (0.91 grams: 31.5%). The prepared solution is heated for 10 hours at 80° C. to produce aluminum-containing active polymer having a relatively low molecular weight and size (i.e., enhanced antiperspirant efficacy active) relative to that of the same solution if not subjected to such prolonged heating. Approximately 34.40 grams of an aqueous solution containing solubilized zirconium hydroxy chloride glycine (Zr 14.68%, Cl 8.18%, Glycine 12.07%) and 11.22 g of butylene glycol are added to the heated aluminum-containing solution. The resulting aluminum-zirconium active solution is then immediately (i.e., within 0–2 hours after preparation) subjected to spray drying on a Buchi 190 Mini Spray Dryer (Brinkman Instruments, Westbury, N.Y., USA) with an outlet temperature of from 88° C. to 90° C. and an inlet temperature that remains at about 237° C. The feed and other spray drying parameters are controlled to maintain the desired outlet temperature. The spray dried product or crystals are collected in a receiver as a crystalline powder with a chloride content of from 14.42% to 14.58% by weight of the collected product.

The spray dried product is then combined with 1,2-hexanediol under ambient conditions and subjected to high-shear mixing for a period of about 16 hours. The resulting mixture is allowed to stand for several hours before filtering out any remaining solids to form a light yellow colored transparent solution. Various combinations of spray dried product and 1,2-hexanediol are mixed together to form anhydrous aluminum zirconium active solutions having varied active concentrations at 1%, 5%, 10%, 15%, 20% and 26%, by weight of the anhydrous solution.

All of the above dissolution process steps for the various active concentrations are repeated but without high shear mixing, but each dissolution under such conditions takes substantially longer than with high shear mixing.

All of the above dissolution process steps for the various active concentrations are also repeated by heating the dissolution solvent (1,2-hexanediol) to between 50° C. and 60° C. to reduce the dissolution time to substantially less than about 16 hours.

All of the anhydrous aluminum-zirconium antiperspirant active solutions exemplified above are applied topically to the underarm area of the skin as a finished antiperspirant consumer product to provide antiperspirant and deodorant efficacy to the applied area of the skin. The applied compositions are clear or translucent, provide little or no visible residue during and after application. All of the exemplified solutions are also used as manufacturing intermediates in formulating finished antiperspirant consumer products comprising solubilized antiperspirant active in solid, semi-solid and liquid forms.

What is claimed is:

1. A process of making stable antiperspirant active solutions, which process comprises the steps of:
   (A) preparing an aqueous solution comprising an aluminum-containing antiperspirant active, water, and an anhydrous solvent having a solubility parameter of from about 9 $(cal/cm^3)^{0.5}$ to about 15 $(cal/cm^3)^{0.5}$;
   (B) spray-drying the aqueous solution to form a solid powder comprising aluminum-containing antiperspirant active and the anhydrous solvent; and
   (C) dissolving the solid powder in a second anhydrous solvent at a temperature of not more than 85° C. the second anhydrous solvent comprising a 1,2-diol solvent having at least 4 carbon atoms, to form a stable anhydrous antiperspirant active solution comprising solubilized aluminum-containing antiperspirant active and the 1,2-diol solvent.

2. The process of claim 1, wherein the aluminum-containing antiperspirant active prior to spray drying is heated to a temperature of at least about 50° C. for a period of time sufficient to enhance the efficacy of the antiperspirant active.

3. The process of claim 2, wherein the aluminum-containing antiperspirant active is heated prior to spray drying at a temperature of from about 70° C. to about 100° C. for at least about 10 hours.

4. The process of claim 1, wherein the process further comprises the step of adding zirconium-containing active solution with the anhydrous solvent and the aluminum-containing antiperspirant active and spray drying the resulting combination to form a solid powder comprising aluminum and zirconium-containing antiperspirant active and anhydrous solvent.

5. The process of claim 4 wherein the weight ratio of the 1,2-diol solvent to the combined zirconium-containing and aluminum-containing antiperspirant active is from about 1:2 to 20:1.

6. The process of claim 4 wherein the weight ratio of the 1,2-diol solvent to the combined zirconium-containing and aluminum-containing antiperspirant active is from about 2:1 to about 4:1.

7. The process of claim 1 wherein the anhydrous solvent has a solubility parameter of from about $10(cal/cm^3)^{0.5}$ to about 13 $(cal/cm^3)^{0.5}$.

8. The process of claim 1 wherein the anhydrous solvent is liquid under ambient conditions and is selected from the group consisting of ethylene glycol, propylene glycol, polyethylene glycol liquids, dipropylene glycol, diethylene glycol, hexylene glycol, butylene glycol, 1,2-pentanediol, hexylene glycol, 1,2-propylene glycol, 1,3-propylene glycol, 1,2-hexanediol, 2-ethyl-1,3-hexanediol, 1,2,6-hexanediol, ethanol, tripropylene glycol, propylene glycol methyl ether, isopropyl glyerol ether, dipropylene glycol methyl ether and combinations thereof.

9. The process of claim 1 wherein the anhydrous solvent comprises butylenes glycol.

10. The process of claim 1 wherein the aluminum-containing antiperspirant active is selected from the group consisting of aluminum halide, aluminum chlorohydrate, aluminum hydroxyhalides, and combinations thereof.

11. The process of claim 4 wherein the zirconium-containing antiperspirant active is selected from the group consisting of zirconyl oxyhalides, zirconyl hydroxyhalides, and combinations thereof.

12. The process of claim 4 wherein the atomic ratio of aluminum to zirconium is from about 0.25:1 to about 5:1.

13. The process of claim 4 wherein the atomic ratio of aluminum to zirconium is from about 0.5:1 to about 2:1.

14. The process of claim 1 wherein the metal to chloride atomic ratio is from about 6.73 to about 2.1.

15. The process of claim 1 wherein the second anhydrous solvent is a 1,2-diol having at least 4 adjacent carbon atoms and which conforms to the formula:

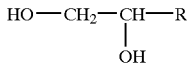

wherein R is an amide, ester, alkyl, ether or silicon-containing moiety, each moiety containing at least 2 carbon atoms.

16. The process of claim 1 wherein the second anhydrous solvent is selected from the group consisting of 1,2-butanediol; 1,2-pentanediol; 4-methyl-1,2-pentanediol; 2-methyl-1,2-pentanediol; 3,3-methyl-1,2-butanediol; 4-methyl-1,2-hexanediol; 1,2-heptanediol; 3-phenyl-1,2-propanediol; 1,2,6-hexanetriol; 1,2-hexandiol; 1,2,4-butanetriol; glycerol isopropyl ether; glycerol propyl ether; glycerol ethyl ether; glycerol methyl ether; glycerol butyl ether; glycerol isopentyl ether; diglycerol isopropyl ether; diglycerol isobutyl ether; diglycerol; triglycerol; triglycerol isopropyl ether; acetic acid glycerol ester; propanoic acid glycerol ester; butanoic acid glycerol ester; 3-methyl butanoic acid glycerol ester; and 3-trimethylsily-1,2-propane diol; silicone-containing 1,2-diols; and combinations thereof.

17. The process of claim 1 wherein the second anhydrous solvent comprises 1,2-hexanediol.

18. The process of claim 1 wherein the resulting stable anhydrous antiperspirant active solution contains less than 10% by weight of water.

19. The process of claim 4 wherein the resulting stable anhydrous antiperspirant active solution contains less than 10% by weight of water.

20. The process of claim 1 wherein the aqueous solution of step (A) comprises
   (a) from about 20% to about 60% by weight of the anhydrous solvent;
   b) from about 5% to about 50% by weight of water; and
   (c) from about 10% to about 30% by weight of the aluminum-containing antiperspirant active.

21. The process of claim 1 wherein the solid powder of step (B) comprises
   (a) from about 10% to about 40% by weight of the aluminum-containing antiperspirant active;
   (b) from about 5% to about 40% by weight of the anhydrous solvent;
   (c) from about 5% to about 20% by weight of water.

22. The process of claim 1 wherein the stable anhydrous antiperspirant active solution of step (C) comprises:
   (a) from about 5% to about 26% by weight of the solubilized aluminum-containing active, and
   (b) from about 5% to about 50% by weight of the 1,2-diol solvent.

* * * * *